(12) United States Patent  
Hallen (10) Patent No.: US 7,314,469 B2  
(45) Date of Patent: Jan. 1, 2008

(54) OBSTETRIC VACUUM EXTRACTOR

(75) Inventor: Jan Ake Hallen, Sävedalen (SE)

(73) Assignee: Medela Holding AG, Baar (CH)

( * ) Notice: Subject to any disclaimer, the term of this patent is extended or adjusted under 35 U.S.C. 154(b) by 775 days.

(21) Appl. No.: 10/650,492

(22) Filed: Aug. 29, 2003

(65) Prior Publication Data

US 2004/0111098 A1 Jun. 10, 2004

(30) Foreign Application Priority Data

Sep. 2, 2002 (SE) .................................. 0202601

(51) Int. Cl.  
*A61B 17/42* (2006.01)
(52) U.S. Cl. ........................................... 606/123
(58) Field of Classification Search ............... 606/121, 606/122, 123, 124; 604/74  
See application file for complete search history.

(56) References Cited

U.S. PATENT DOCUMENTS 4,512,347 A     4/1985  Uddenberg  
4,620,544 A    11/1986  O'Neil  
4,730,617 A *   3/1988  King ........................... 606/123  
5,957,931 A     9/1999  Dimitriu  
6,361,542 B1 *  3/2002  Dimitriu et al. ............ 606/123

FOREIGN PATENT DOCUMENTS

GB       2296868        7/1996

* cited by examiner

*Primary Examiner*—Kevin T. Truong  
(74) *Attorney, Agent, or Firm*—Gauthier & Connors LLP (57) ABSTRACT

The present invention relates to an obstetric vacuum extractor comprising a suction cup of a hard material, which suction cup is provided connection for a tube and a connector piece. The vacuum extractor further comprises a towing means of a flexible material as well as a locking means. The towing means comprises a handle, a connecting part and a connector. The invention is characterized in that said connector piece is an integrated part of the suction cup. Said connector is arranged to be brought to attachment in said connector piece, said connector piece and connector being movably fixable to each other.

21 Claims, 7 Drawing Sheets

OBSTETRIC VACUUM EXTRACTOR

TECHNICAL FIELD

The present invention relates to an obstetric suction device, a so called vacuum extractor, comprising a suction cup of a hard material, which suction cup is provided with connection for a tube and a connector piece, whereby the suction device further comprises a towing means of a flexible material as well as a locking means. The towing means comprises a handle, a connecting part and a connector.

BACKGROUND AND THE PROBLEM

Delivery may in certain cases not be finished in a natural way, but assistance in the form of different aid means is needed. Obstetric suction devices are used as aid means at deliveries. The indication of use may be fetal distress, fetus problems, which may e.g., show in a weakened pulse of the fetus due to insufficient or closed oxygen addition through the placenta. Further indications of use may e.g., be a prolonged delivery period of the mother and condition of the mother requiring a shortened delivery period. Certain conditions are required for using obstetric suction devices. For example, the child must be fully-developed, 34 weeks old or older, further the amnion must be broken and the external os uteri be fully dilated.

There are mainly two types of obstetric suction devices, those made of flexible materials, such as e.g., soft polymers, or rubber, alternatively, and those made of hard materials, such e.g., hard polymers or metal, e.g., stainless steel or brass, alternatively.

In U.S. Pat. No. 4,512,347 a hard obstetric suction device is described being made of metal, preferably stainless steel. The suction device comprises a suction cup, which is provided with connector piece in which connector piece a connecting part, e.g., a chain of fixedly secured. The suction device further comprises a handle which handle is releasably provided to the connecting part. This suction device is expensive to produce and is thought to be used multiple times.

Further, U.S. Pat. No. 4,620,544 describes a suction device comprising a suction cup, and a connection means. The suction cup is made of metal. On the sphere of the suction cup a rotating disc is provided, which rotating disc is provided with a transverse bar, which bar is attached to the disc at both its ends. On the transverse bar a ring is attached and in the ring the connecting part, a chain or similar means arranged. The chain serves as a connecting part and handle. Said rotating disc may create a cutting edge, which can hurt the other. Further, the suction cup is high and hard to clean. A soft obstetric suction device consisting of silicon of medical quality is described in WO 89/06112. The instrument is made in one piece and consists of a handle and a suction cup. The suction cup is available in two sizes having 50 and 60 mm innerdiameter respectively. The expected life length of a suction device according to WO 89/06112 is about two years, or 30 sterilisations in an autoclave at 134° C. for three minutes, alternatively. Said suction cup is an external os uteri instrument which can not be used at all operations.

U.S. Pat. No. 5,224,947 describes an obstetric vacuum extractor comprising a suction cup and a connecting part. The suction cup is made of a soft material and the connecting piece in a semi-hard material. In the connecting piece, which inter alia is made of a tubular element, a tube is arranged to which tube a vacuum pump is connected. This contruction is not durable at practical use.

U.S. Pat. No. 6,074,399 describes an obstetric vacuum extractor comprising a suction cup, handle and a manually maneuovered vacuum pump, which parts are delivered as one unit. The suction cup is made of a flexible or harder material, alternatively. The suction cup or the whole device, alternatively, can be made as a disposable unit. The hand pump and the handle can be made for reuse. The invention above requires a specially contrued pump, in the form of a hand pump, which leads to complicating the manufacturing process. The manufacture is further expensive, in particular when the suction device is made as a disposable one, leading to an expensive product when bought. The hand pump leads to fact that the product can not be connected and used together with standard tubes.

U.S. Pat. No. 6,059,795 describes a suction device which is characterized in that a recess is arranged on the sphere of the suction cup. The tube connected to the vacuum pump is lowered into the recess which provides for a smooth sphere of the suction cup and which further provides for aplication of the suction device in complicated positions.

The present invention discloses how one arranges a towing means to the suction cup. The invention provides an obstetric vacuum extractor totally made of polymeric materials having different properties adapted to what is being required for the suction cup and the towing means, respectively. The towing means comprising handle connecting part and connector can be made in one piece. The suction cup and the towing means are releasably arranged to each other but simultaneously can be fixed to each other by means of a locking means for maximum security at use. At the manufacture the suction cup is preferably injection-moulded as such and the towing means as such. Then the suction cup and the towing means are mounted together to one suction device and are packed and sterilized. At use the suction device is connected to a vacuum pump via a tube connection by means of a tube.

THE OBJECTIVES AND THE SOLUTION TO THE PROBLEM

The object has been to solve the above described problem by obtaining a disposable obstetric vacuum extractor made of a hard material comprising a suction cup provided with a tube connection, and a connection means, further comprising a towing means and a locking means. The towing means comprises a handle, a connecting part and a connector, which parts can be made in one piece. The suction cup is made of a hard material and the towing means in a flexible, non-elastic material. The suction cup and the towing means, comprising handle, connecting part and connector are made of disposable polymer materials. The suction cup is made of hard polymer, such as a polycarbonate having formstable properties. The towing means is e.g., made of a flexible plastic material which does not provide stretching but which is readily bent.

This has been solved in that the connector piece has been made as an integrated part of the suction cup, preferably arranged on the sphere of the suction cup, said connecting part is arranged to be brought to fixation to said connector piece, said connector piece and connecting part being movably fixed to each other.

Advantages of the invention are that

It is a disposable product which is thrown away after use, which is rational, hygienic and cost saving, as one need not to clean and sterilize the product costs will be kept down.

Handle, connecting part and connector can be made in one piece, the handle and the connector can be made tubular.

The connecting part can be made in different lengths and in such away the sd can be adapted to different needs and desire.

The connector can be varied, e.g., having the form of a ball which can rotate in all directions or having the form of a cylinder which moves radially in the connector piece but not sidewards.

The locking means can be varied and be adapted to different solutions, which improves security in connection with the use of the sd.

It is cheap, simple and time efficient to produce the sd, which in turn means that the price of the product can be kept low.

It is arranged in such a way that the suction cup release from the suction cupalp of the fetus when the traction force >20 kg, which is a safty mechanism not to damage the fetus and the mother.

It can be connected to standard tubes and pumps via a tube connection, which means that no specially designed constructions are needed.

BRIEF DESCRIPTION OF THE DRAWING

In the following the invention will be described more in detail with reference to some embodying examples and with reference to the accompanying drawing, wherein.

DESCRIPTION OF EMBODIMENTS

In the following some preferred embodiments of the invention will be described in more detail with reference to the figures of said drawing.

In accordance with all embodiments described below the obstetric vacuum extractor of the present invention comprises a suction cup, which in all figures of the drawing is denoted 1. Further the sd a towing means 6, comprising a handle 7, a connecting part 8 and a connector 9, which parts can be made in one piece. Further the same denotations are used in all figures for the same parts.

The suction cup 1 has a substantially smooth outer surface, provided with substantially peripherally arranged reinforcing edge 2, which is preferably well rounded. The inner side of the suction cup 1 is substantially smooth, as well. Within the suction cup 1 a releasable bottom mplate 14 arranged, having the form of a net in any kind of polymer material. The bottom plate 14 distributes the suction force over the whole inner surface of the suction cup 1, to prevent a sticking against the scalp of the fetus. The suction cup 1 comes mainly in three different sizes having 40, 50, and 60 mm innerdiameter, respectively. The hard suction cup 1 will not become deformed, which means that one obtains a maximum adherence. On the suction cup 1, preferably on the sphere 3 of the suction cup there is a connector piece 4 substantially fixedly arranged for fastening the towing means 6. On the sphere 3 of the suction cup there is further a tube connector 5 arranged, which tube connector 5 connects the suction cup 1 with a vacuum pump by means of a substantially releasably arranged tube.

According to a first embodiment, FIG. 1 a-e the handle is hollow and tubular. The connecting part 8 is in the form of a string. The connecting part 8 is further bendable sidewise but can not be stretched in a longitudinal direction. The connector 9 is a massive or hollow ball, alternatively.

The connector piece 4 is fixedly arranged and integrated onto the sphere 3 of the suction cup and provided with slot 10. The connector piece 4, which in this embidment is present in the form of a casing is further provided with a substantially part spherical inner surface 15. The connector 9 in this case in the form of ball is introduced into the connector piece 4 whereby the connecting part 8 runs into the slot 10. The thickness of the connecting part 8 is somewhat smaller than the width of the slot 10 to allow for an unimpeded run of the conecting part 8 in the slot 10. The tube connector 5 is fixedly arranged on the sphere 3 of the suction cup.

The outer diameter of the ball is somewhat smaller than the inner diameter of the connector piece 4 leading to an allowance between the inner diameter of the connector piece 4 and the outer diameter of the ball. This leads to in turn that the ball can be readily introduced into the connector piece 4 and that it is movable in all directions. The walls inside the connector piece 4, the casing, is preferably made of part spherical surfaces 15, leading to the formation of a ball joint inside the connector piece 4 which in turn provides for advantages when it comes to tensile strength.

The sd is further arranged in such a way that the suction cup 1 will release from the scalp of the fetus at traction forces >20 kg, which is a safety measure mechanism not to hurt the fetus or the mother.

A locking means 11 is provided in the opening of the connector piece so that the connector 9 should not slide out off the connector piece 4. According to a first embodiment the locking means 11 is a fixable, locking unit in the form of a plug which will become fastened in the opening of the connector piece when the connector 9 has been brought into the connector piece 4. The locking means 11, the plug, is then secured snapping it or glueing it threto. The locking means 11, the plug, has a part spherical end surface 16 to make it fit with the sphere of the connector 9, the ball.

In order for the towing means 6 not to be a hinder when the suction cup is used the locking means 11, the plug, or the connector piece 4, alternatively, be arranged to receive part of the connecting part 8 so that the handle 7 can be bent down. According to one variety, FIG. 1d, the locking means 11, the plug, is provided with a slot 18. The slot 18 is radially directed from the jacket and inwardly and axially running along the locking means 11. At the introduction of the suction cup 1 the connecting part 8 may be partly received by the slot 18 whuich facilitates the introduction and provides for that the suction cup 1 can be brought further in towards the head of the child to be delivered. According to a further variety, FIG. 1e, the connector piece 4 comprises a recess 19 provided in one of its ends, in which recess 19 the connecting part 8 can be partly received.

At the introduction of the obstetric vacuum extractor the suction cup 1 is brought against the head of the child. At the introduction the sd is finally mounted which means that the connector 9 as been introduced into the connector piece 4. Then The connector 9 and the connector piece 4 being movably fixed to each other by means of the locking means 11.

According to the first embodiment the handle 7 is hollow and tubular, but may of course take other shapes, e.g., being in the form of a ball, disc or cone and being massive. The connecting part 8 is string shaped but may also take other shapes, e.g., being in the form of a band or being a chain. The connector 9 is a massive or hollow ball, alternatively, but may also take the shape of a cylinder or cone.

The connector piece 4 is according to the first embodiment fixedly integrated onto the sphere 3 of the suction cup but may also be provided releasably. The conector piece 4 is further provided with a substantially part spherical inner surface 15 which inner surface 15 of course may have another shape, as well, inter alia depending on the shape of the connector 9.

The locking means 11 is provided in the opening mof the connector piece and according to the first embodiment the locking means 11 is a fixable, locking unit in the form of plug which is fixed in the connector piece 4, but may of course also be a pin or the similar. The locking means 11 is a snappable or glueable unit, according to the embodiment, but may also be welded or rivetted, or the similar. The locking means 11, the plug, has, further, a part spherical end surface 16 to fit with the sphere of the connector 9, the ball, but the end surface may of course take any other shape inter alia depending on the shape of the connector 9.

Figure 1A:
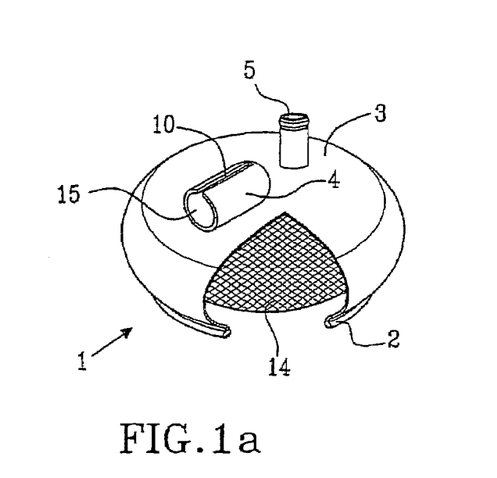
FIGS. 1a-e shows schematically the invention according to a first embodiment.
Figure 1B:
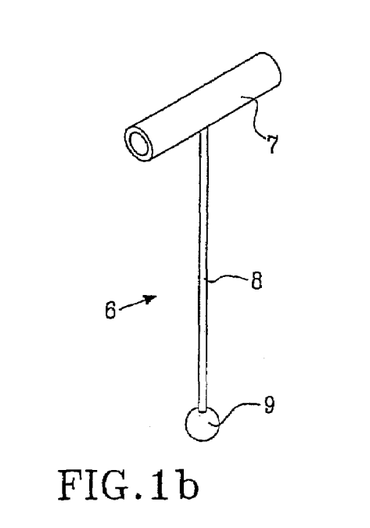
Figure 1C:
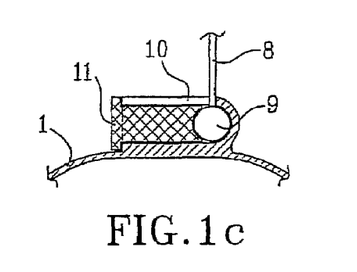
Figure 1D:
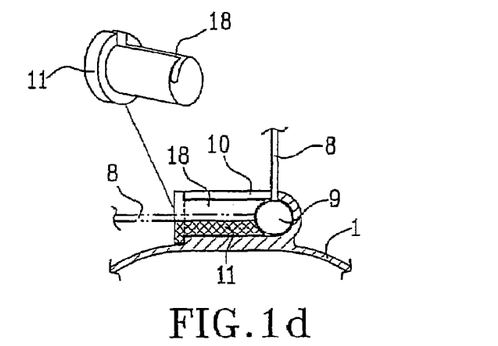
Figure 1E:
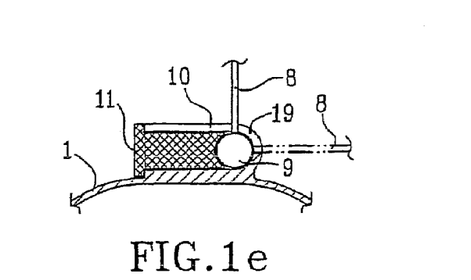
Figure 2:
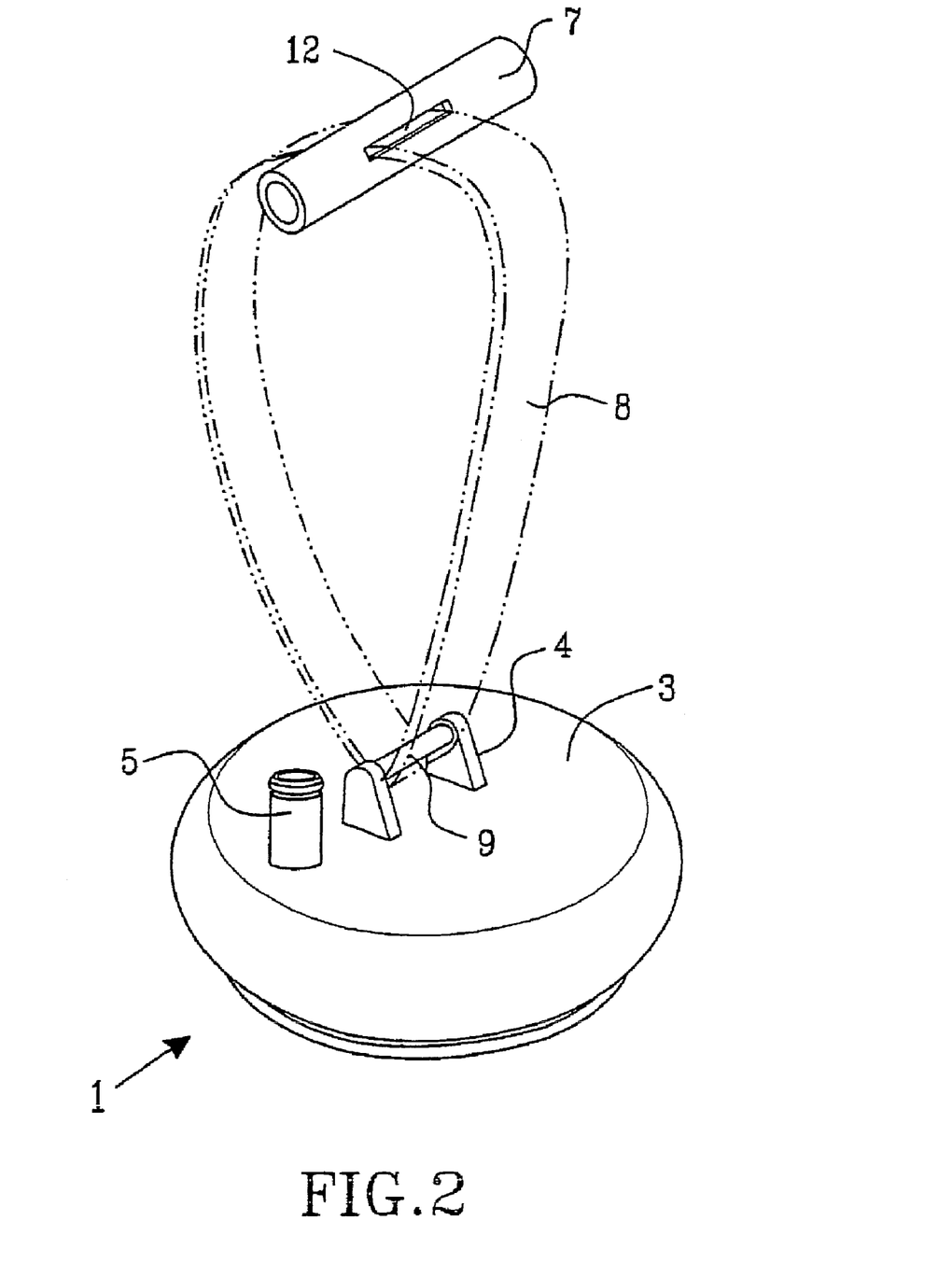
FIG. 2 shows schematically the invention according to a second embodiment.

According to a second embodiment, FIG. 2, the handle 7 being hollow and tubular, is provided with a slotted hole 12 transverse to the longitudinal axis of the handle 7. The connecting part 8 is a polymer ribbon, preferably a flat, injection moulded ribbon, which is welded by means of an ultrasonic weld.

The connector piece 4 of the sphere 3 of the suction cup consists of two fittings at a distance from each other, which distance is greater than the width of the connecting part 8, the ribbon. Between the fittings a cross bar is provided, which in this embodiment serves as a connector, somewhat above the surface of the sphere 3 of the suction cup, so that the connecting part 8, the ribbon, can be brought in between the surface of the sphere 3 of the suction cup and the connector 9, the cross bar. The length of the connecting part 8, the ribbon, may be adjusted by rolling it onto the handle 7.

The suction cup 1 is moulded as such with the connector piece 4 fixedly provided onto the sphere 3 of the suction cup. The connector 9 is integrated and fixedly arranged to the connector piece. Further the handle is moulded as such. The parts are then brought together by means of the connecting part 8 and are welded together, preferably using an ultrasonic welding.

According to the second embodiment the handle 7 is hollow and tubular but may of course e.g., be formed as a ball, cone or the similar and e.g., be massive. The handle 7 is further provided with a slot shaped hole 12, which of course may be shaped in other ways, e.g., circular, or the similar. The connecting part 8 is a polymer ribbon, preferably a flat, injection moulded ribbon, but may also take other shapes such as string form or be a chain.

Further the connector piece 4 according to the second embodiment consists of two fittings at a distance from each other, whereby the connector piece 4 of course may be shaped in any other way or consist of a casing, or the similar. The parts are joined, according to the second embodiment, to each other by means of the connecting means 8 and are welded, preferably using an ultrasonic welding, but may of course be fixed using glue, rivets or the similar.

Figure 3:
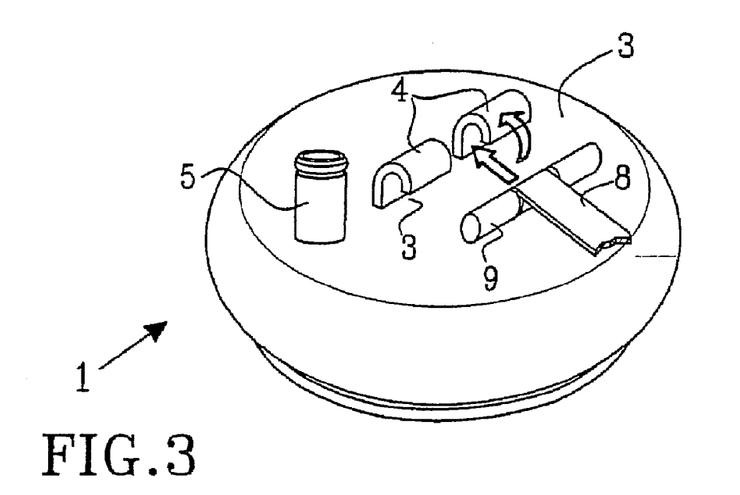
FIG. 3 shows schematically the invention according to a third embodiment.

According to a third embodiment, FIG. 3, the handle 7 (not shown) is hollow and tubular and is provided with a slot shaped hole 12 (not shown). The connecting means 8 is a ribbon, e.g., a flat, injection moulded ribbon. The connector 9 is a hollow, cylindrical bar around which bar the connector 8 is e.g., wrapped attached thereto by means of an ultrasonic welding or attached thereto in accordance with the second embodiment above. The connector 9, the bar, is somewhat longer than the width of the connecting means 8, the ribbon, which means that the connector 9, the bar projects somewhat on either side of the connecting means 8, the ribbon.

The connector piece 4 provided on the sphere 3 of the suction cup comprises two, preferably arcuate fittings, which are connected to the surface of the sphere 3 of the suction cup. In one end the connector piece 4, the fittings, is attached directly to the surface and in the other end there is a small distance between the fittings and the surface of the sphere 3 of the suction cup. Said dsistance is somewhat smaller than the connector 9, for snapping the connector 9 in. The connector 9 may e.g., be finished with a flange in both ends. The distance between the two fittings is somewhat greater than the width of the connecting means 8, the ribbon. The connector 9 and the connecting means 8 wrapped around it, is introduced into the connector piece 4 so that the projecting ends of the connector 9, the bar, will pass beneath the fittings. The connector 9 and the connecting means 8 are then bent upwardly and is snapped to attach but will still become rotatable.

According to the third embodiment the handle 7 is hollow and tubular but may also be shaped as a ball, a cone or the similar. The handle 7 is further provided with a slot shaped hole 12, which also may be shaped as circle, a cone or the similar. The connecting means 8 is a ribbon, e.g., a flat, injection moulded ribbon, but may also take other shapes such as string form or be a chain. The connector 9 is a hollow, cylindrical bar, but may also, e.g., be massive and be a ball or the similar.

The connector piece 4 is provided on the sphere 3 of the suction cup and comprises preferably two arcuate fittings which fittings of course may be designed in other ways and e.g., be any casing or the similar.

Figure 4:
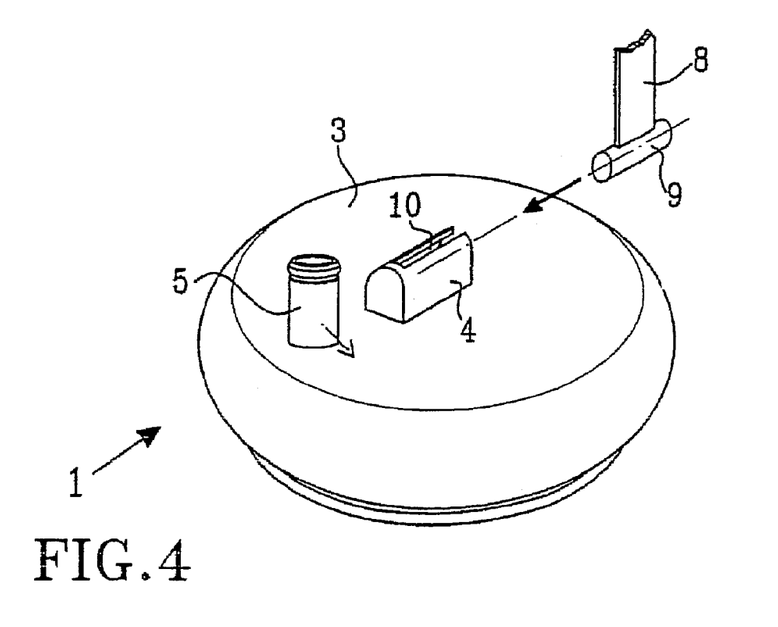
FIG. 4 shows schematically the invention according to a fourth embodiment.

According to a fourth embodiment, FIG. 4, the handle 7 (not shown) is hollow and tubular. The connecting means 8 is a ribbon and the conector 9 is a cylindrical, massive or hollow bar.

The connector piece 4 of this embodiment is a substantially cylindrical casing arranged to the sphere 3 of the suction cup, the cylindrical casing being provided with a slot 10. The connector 9 is introduced into the slot 10. The locking means 11 (not shown) may e.g., consist of a glueable plug or the similar. The outer diameter of the cylindrical connector 9 is somewhat less than the inner diameter of the connector piece 4, the casing, and the thickness of the connecting means 8, the ribbon is somewhat less than the width of the slot 10.

According to the fourth embodiment the handle 7 is hollow and tubular, but may also be shaped in other ways, e.g., be massive and shaped as a ball or a cone. The connecting means 8 is a ribbon, but but may also take other shapes such as string form or be a chain. The connector 9 is a cylindrical, massive or hollow bar, but may also be a ball, a cone or the similar.

The connector piece 4 is, in this fourth embodiment, a substantially cylindrical casing, but may also be shaped in any other suitable way, as e.g., in the form of one or more fittings.

The locking means 11 may e.g., consist of a glueable plug or the similar, but the parts may also be kept together by means of welding, rivets, or the similar.

Figure 5:
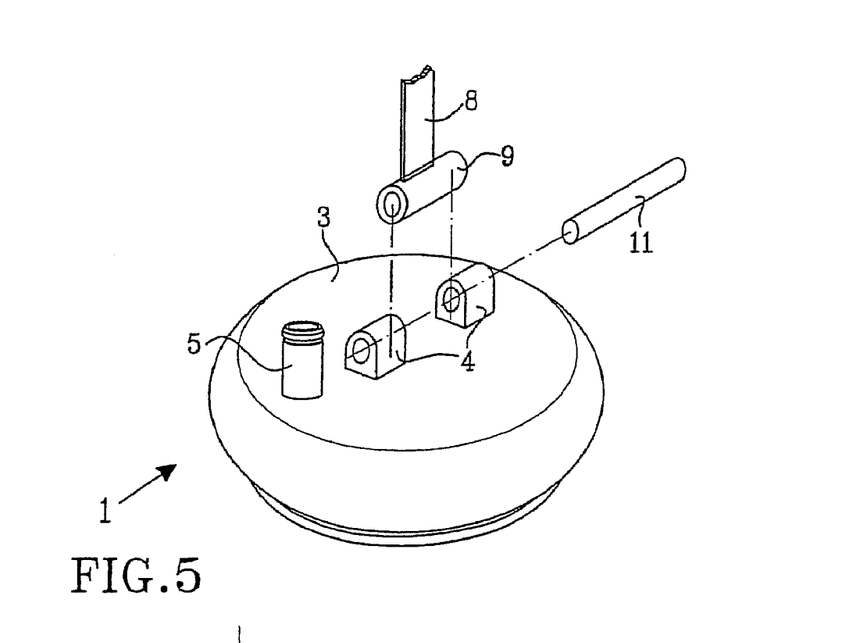
FIG. 5 shows schematically the invention according to a fifth embodiment.

According to a fifth embodiment, FIG. 5, the handle 7 (not shown) is hollow and tubular. The connecting means 8 is a ribbon and the connector 9 is a substantially cuylindrical hollow bar.

The connector piece 4 comprises two fittings, provided on the sphere 3 of the suction cup. The distance between the fittings is msomewhat greater thanm the width of the connecting means 8, the ribbon. The fittings are attached to the surface of the sphere 3 of the suction cup. The dsistance between the fittings is somewhat greater than the size of the connector 9, the cylinder. The connector is introduced between the fittings.

The locking means 11 is in this embodiment a pin which is brought into, primarily through one of the fittings and then through the connector 9 and finnaly through the second fitting. The locking means 11, the pin, has substantially the same length as the common length of the fittings and the connector 9. The locking means 11, the pin, is provided with grooves in order to lock against the connector 9.

According to the fifth embodiment the handle 7 is hollow and tubular, but may also be shaped in other ways, e.g., be massive and shaped as a ball or a cone. The connecting means 8 is a ribbon, but but may also be a chain or a string formed unit. The connector 9 is a substantially cylindrical hollow bar, but may also be substantially round or conical, massive unit or the similar.

The connector piece 4 comprises two fittings, provided on the sphere 3 of the suction cup, but the connector piece 4 may also be e.g., one fitting or a casing or the similar. The locking means 11 is, in this fifth embodiment, a pin, but may also be a plug, an ultrasound weld or the similar.

Figure 6:
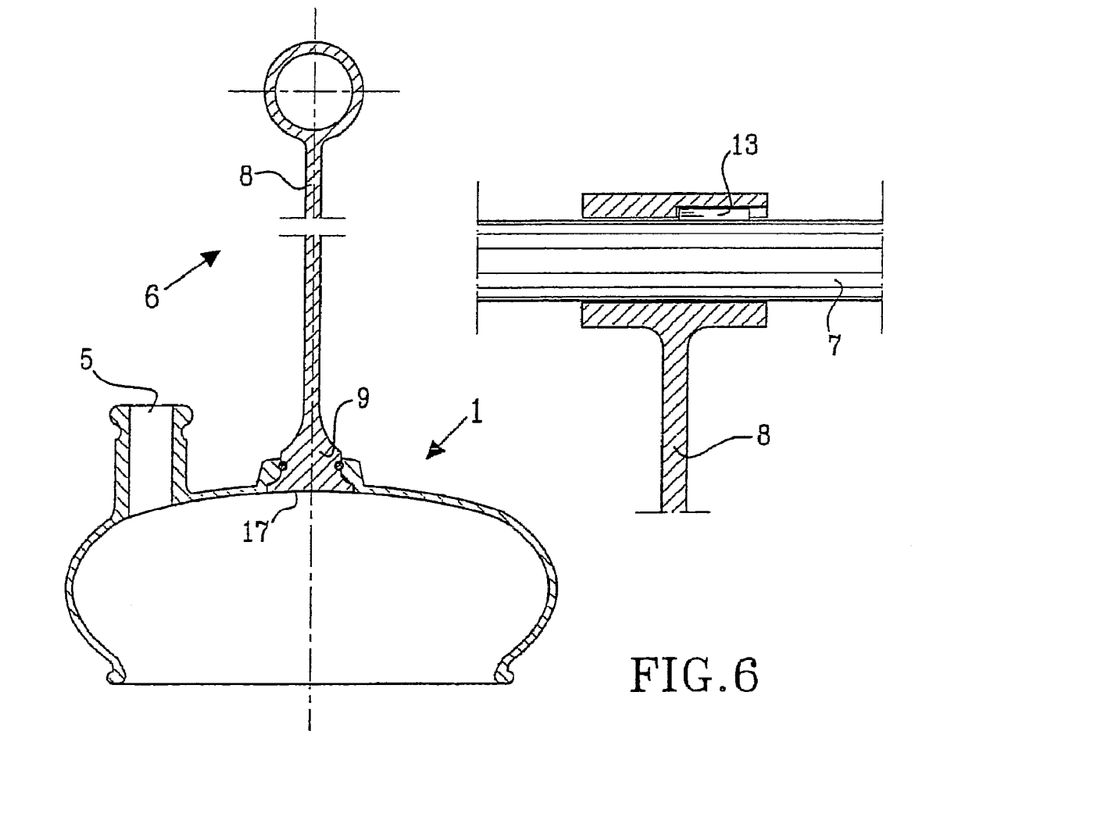
FIG. 6 shows schematically the invention according to a sixth embodiment.
Figure 7A:
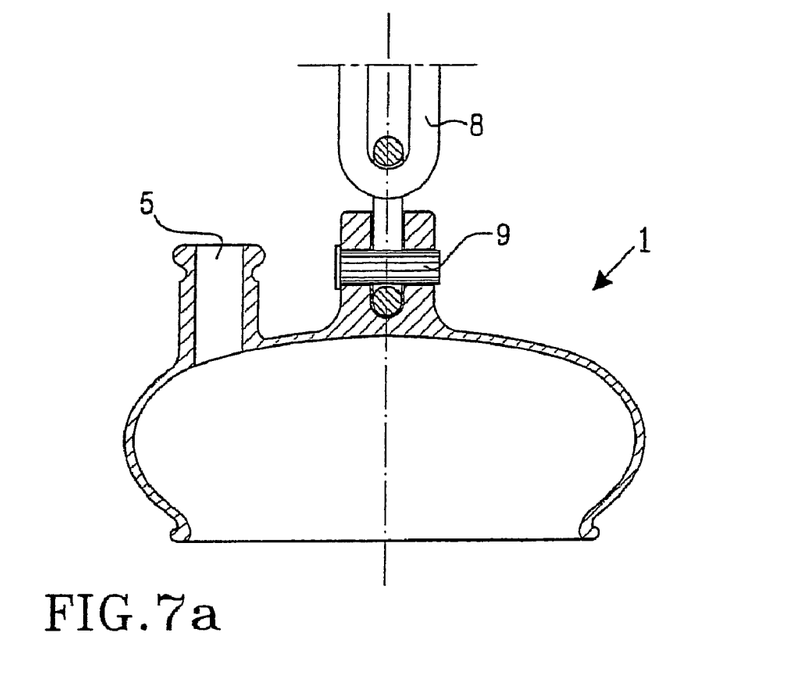
FIG. 7a-f shows schematically the invention according to further embodiments.
Figure 7B:
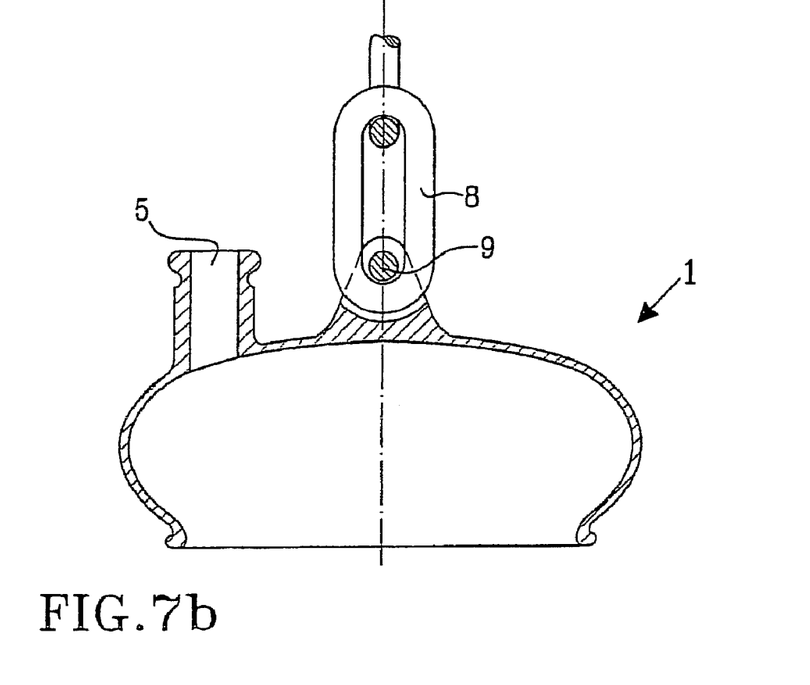
Figure 7C:
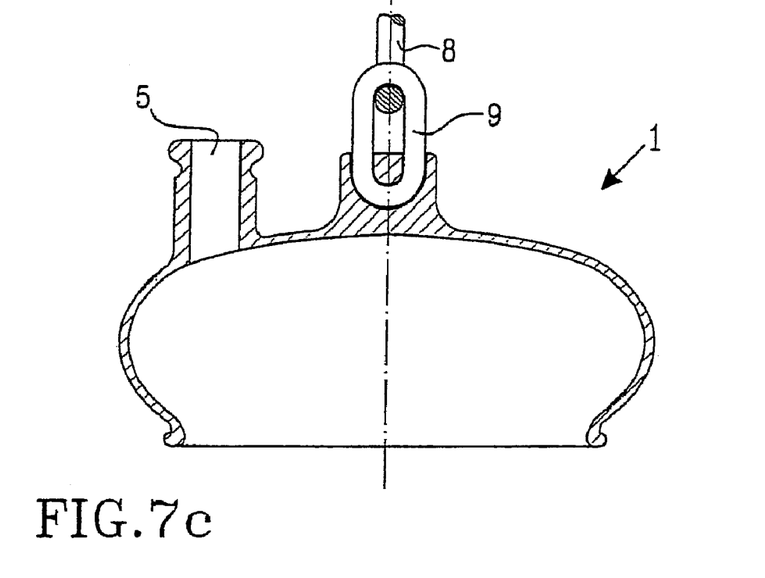
Figure 7D:
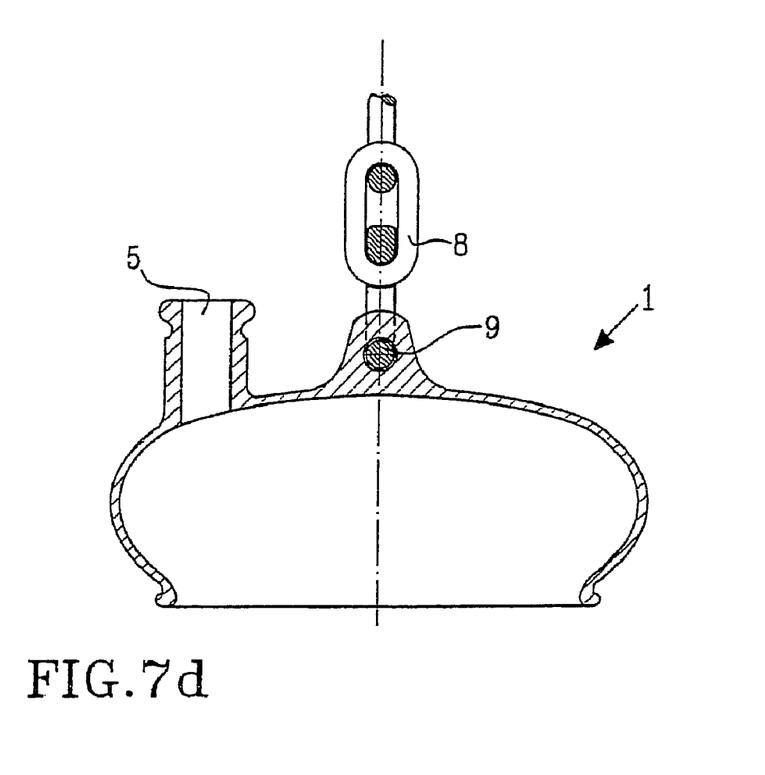
Figure 7E:
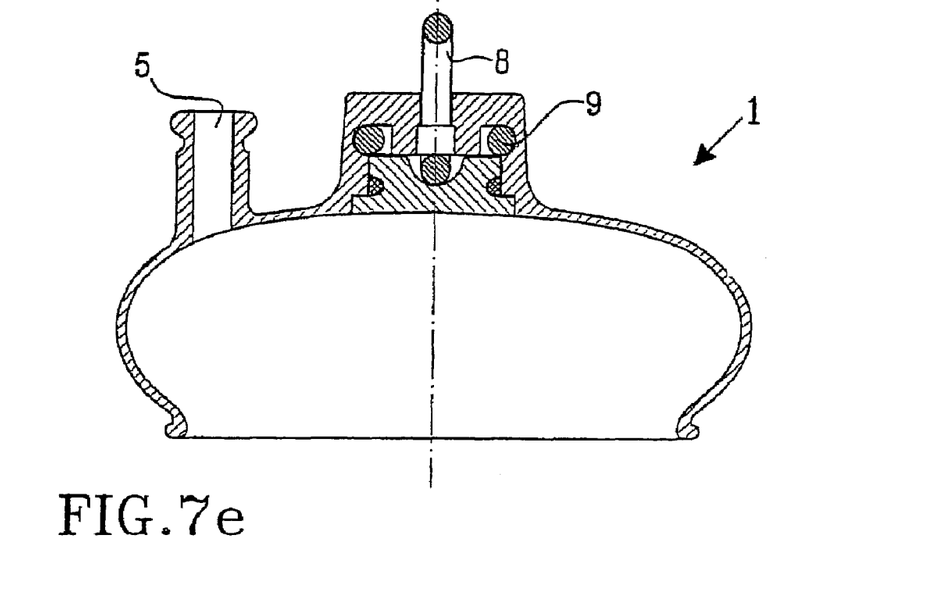
Figure 7F:
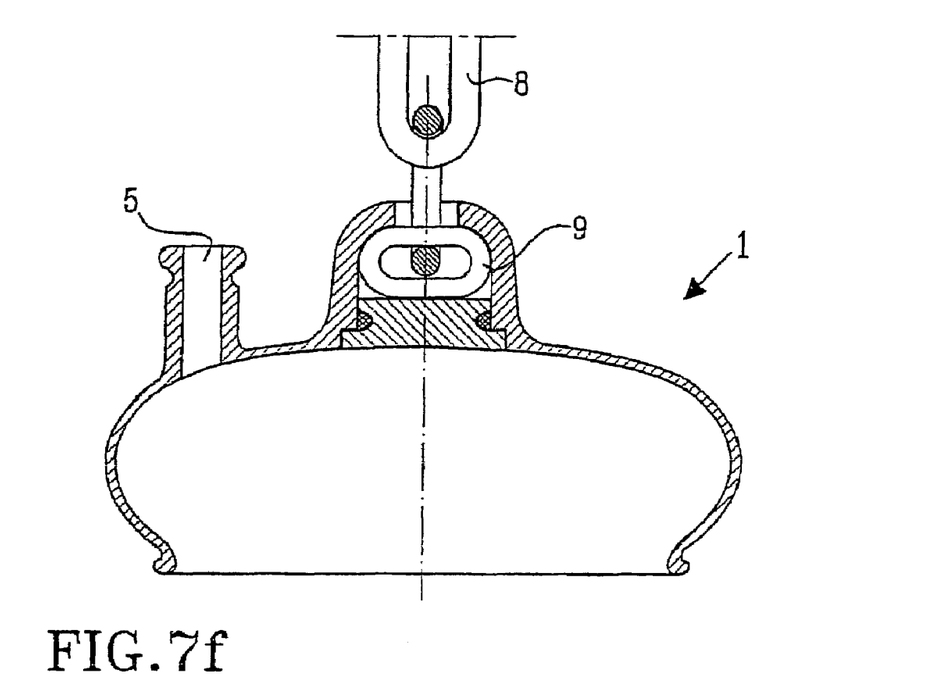

According to a sixth embodiment, FIG. 6, the handle 7 is a hollow, grooved and resilient cylinder provided with a stop lug 13. The connecting means 8 is a ribbon shaped or bar shaped unit. Of the connecting means 8, the ribbon, an loop is made, in which loop the handle 7 is introduced. The stop lug 13 will stop the handle 7 from sliding out of the loop. The suction cup 1 is, according to this embodiment, provided with holes 17 through which the towing means 6 is introduced from beneath and is snapped to attach by means of the connector 9. The connector 9 is a massive substantially cylindrical unit, which is fixed to the throughgoing hole 17 of the sd. Sealing to obtain vacuum is made by means of an O-ring.

According to the sixth embodiment the handle 7 is a hollow, grooved, and resilent cylinder, but may of course be a ball or a cone and e.g., be massive. The handle 7 is further provided with a stop lug 13 stopping the handle 7 from sliding out of the loop, but of course, another stopping means may be used in stead of the stop lug 13, e.g., a snapping means or the similar.

The connecting means 8 is a ribbon shaped or bar shaped unit, which unit of course may be string formed or be a chain.

The connector 9 is a massive, substantially cylindrical unit, but may even be a conical or ball shaped unit and be hollow or partly hollow.

According to further embodiments, FIG. 7 *a-f*, the connecting means 8 is substantially different types of chains, preferably made of hard polymer material. In FIG. 7*a* and /*b*, the connector 9 is a rivet. In FIG. 7*c* the connector 9 is ball moulded into the sphere 3 of the suction cup. FIGS. 7*e* and 7*f* the connector 9 is a chain around own link.

According to the further embodiments the connecting means 8 is mainly different types of chains but may also be string formed or ribbon formed units. The connector 9 is, in the different FIGS. 7*a-f* different units which of course may be varied and combined between the different embodiments.

The present invention has now been described by means of a number of emboodying examples and should be understood that different modifications and complementary additions may be made within the scope of the invention as defined in the accompanying claims.

LIST OF REFERENCE NUMBERS suction cup 1
reinforcing edge 2
sphere of the suction cup 3
connector piece 4
tube connection 5
towing means 6
handle 7
connecting means 8
connector 9
slot 10
locking means 11
slot shaped hole 12
stop lug 13
bottom plate 14
inner surface of connector piece 15
end surface of locking means 16
hole 17
groove 18
recess 19

The invention claimed is:

1. An obstetric vacuum extractor comprising a suction cup of a hard material, having connection for a tube and a connector piece, a towing means of a flexible material as well as a locking means, whereby the towing means comprises a handle, a connecting part and a connector, characterized in that said connector piece is an integrated part of the suction cup, said connector being arranged to be brought to attachment in said connector piece, said connector piece and connector being movably fixable to each other; and wherein said connector is ball shaped.

2. An obstetric vacuum extractor according to claim 1, wherein said handle, said connecting part and said connector are made in one piece.

3. An obstetric vacuum extractor according to claim 1, wherein said handle, said connecting part and said connector are made as separate units.

4. An obstetric vacuum extractor according to claim 1, wherein said connector piece is an integrated part of the sphere of the suction cup.

5. An obstetric vacuum extractor according to claim 1, wherein said connector piece comprises on or more parts.

6. An obstetric vacuum extractor according to claim 1, wherein said connector piece comprises a slot.

7. An obstetric vacuum extractor according to claim 1, wherein said connector piece comprises a recess proved in one of its ends.

8. An obstetric vacuum extractor according to claim 1, wherein said connector piece has a part spherical inner surface.

9. An obstetric vacuum extractor according to claim 1, wherein said connecting means is string formed.

10. An obstetric vacuum extractor comprising a suction cup of a hard material, having connection for a tube and a connector piece, a towing means of a flexible material as well as a locking means, whereby the towing means comprises a handle, a connecting part and a connector, characterized in that said connector piece is an integrated part of the suction cup, said connector being arranged to be brought to attachment in said connector piece, said connector piece and connector being movably fixable to each other; and wherein said locking means is a fixable, locking unit provided in the connector piece.

11. An obstetric vacuum extractor according to claim 10, wherein said fixable, locking unit has a part spherical end surface.

12. An obstetric vacuum extractor according to claim 11, wherein said fixable, locking unit is provided with a radially directed, axially running groove, in which groove part of the connecting means can be received.

13. An obstetric vacuum extractor comprising a suction cup of a hard material, having connection for a tube and a connector piece, a towing means of a flexible material as well as a locking means, whereby the towing means comprises a handle, a connecting part and a connector, characterized in that said connector piece is an integrated part of the suction cup, said connector being arranged to be brought to attachment in said connector piece, said connector piece and connector being movably fixable to each other; and wherein said locking means is a glueable unit provided in said connector piece.

14. An obstetric vacuum extractor according to claim 10 or 13, wherein said handle, said connecting part and said connector are made in one piece.

15. An obstetric vacuum extractor according to claim 10 or 13, wherein said handle, said connecting part and said connector are made as separate units.

16. An obstetric vacuum extractor according to claim 10 or 13, wherein said connector piece is an integrated part of the sphere of the suction cup.

17. An obstetric vacuum extractor according to claim 10 or 13, wherein said connector piece comprises on or more parts.

18. An obstetric vacuum extractor according to claim 10 or 13, wherein said connector piece comprises a slot.

19. An obstetric vacuum extractor according to claim 10 or 13, wherein said connector piece comprises a recess proved in one of its ends.

20. An obstetric vacuum extractor according to claim 10 or 13, wherein said connector piece has a part spherical inner surface.

21. An obstetric vacuum extractor according to claim 10 or 13, wherein said connecting part is string formed.

* * * * *